United States Patent [19]

Leopando

[11] Patent Number: 5,494,828
[45] Date of Patent: Feb. 27, 1996

[54] SLIDE DISPENSING DEVICE AND METHOD

[76] Inventor: Mark E. Leopando, 545 E. Cypress Ave., Unit E, Burbank, Calif. 91501

[21] Appl. No.: 275,282

[22] Filed: Jul. 13, 1994

[51] Int. Cl.[6] .............................. G01N 1/10; C12M 1/34; B01L 3/02; B01L 11/00
[52] U.S. Cl. .................... 436/180; 422/100; 422/101; 435/309.1; 435/40.51; 73/863.32; 73/863.01; 73/864.11
[58] Field of Search .................... 436/180; 435/292; 422/100, 101; 427/2.11, 2.12, 2.13; 73/863.32, 864.01, 864.11; 118/120

[56] References Cited

U.S. PATENT DOCUMENTS

| | | | |
|---|---|---|---|
| 577,362 | 2/1897 | Ettlinger | 239/892 |
| 2,863,319 | 2/1958 | McLin | 422/100 |
| 3,470,847 | 12/1966 | Chapin et al. | 118/100 |
| 4,094,641 | 6/1978 | Friswell | 436/180 |
| 4,334,879 | 6/1982 | Fujimori | 422/100 |
| 4,359,013 | 11/1982 | Prevo | 118/100 |
| 4,378,333 | 3/1983 | Laipply | 422/100 |
| 4,392,450 | 7/1983 | Prevo | 118/120 |
| 4,494,479 | 1/1985 | Drury et al. | 118/120 |
| 4,516,522 | 5/1985 | Drury et al. | 118/120 |
| 4,562,043 | 12/1985 | Mennen et al. | 422/56 |
| 4,721,680 | 1/1988 | Jeffs et al. | 436/180 |
| 4,971,763 | 11/1990 | Columbus | 422/100 |
| 5,030,421 | 7/1991 | Muller | 422/102 |
| 5,063,026 | 11/1991 | Wong | 422/102 |

FOREIGN PATENT DOCUMENTS 0332753  9/1989  European Pat. Off. .

OTHER PUBLICATIONS

Roche Image Analysis Systems prouct description.
Shandon Lipshaw product description.
American Clinical Laboratory Improved Technology for Cytology Specimen Preparation by A. A. Hurley, K. L. Douglas, and D. J. Zahniser—Apr. 1991.
Cyto–Shuttle product and procedure description.

Primary Examiner—Robert J. Warden
Assistant Examiner—N. Bhat
Attorney, Agent, or Firm—Lawrence S. Cohen; Freilich, Hornbaker & Rosen

[57] ABSTRACT

A slide dispensing device is described which has a cone shaped upper portion which is nestable to a conventional cytology pipette, and a lower portion which is fan shaped ending in a long narrow dispensing slot to evenly distribute a specimen material onto a slide. A method is described in which a prepared specimen is aspirated into a pipette; then the pipette is nested to a slide dispensing device which has an upper portion which is nestable to the pipette and a fan shaped lower portion forming a long narrow dispensing slot; then the assembly is placed so that the long narrow dispensing portion is on a slide; and the assembly is moved along the slide while the pipette is squeezed to expel the specimen in an even band on the slide.

14 Claims, 2 Drawing Sheets

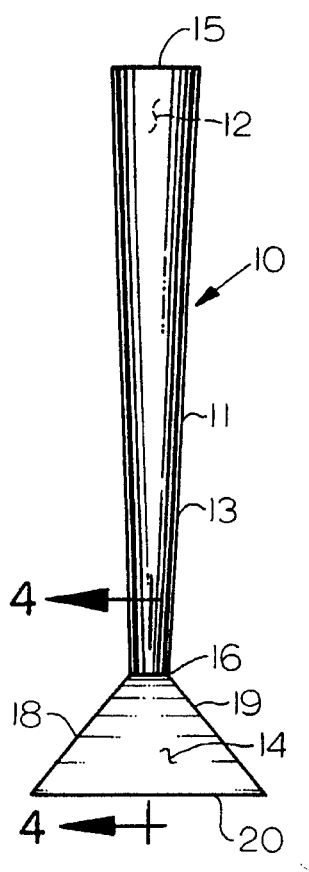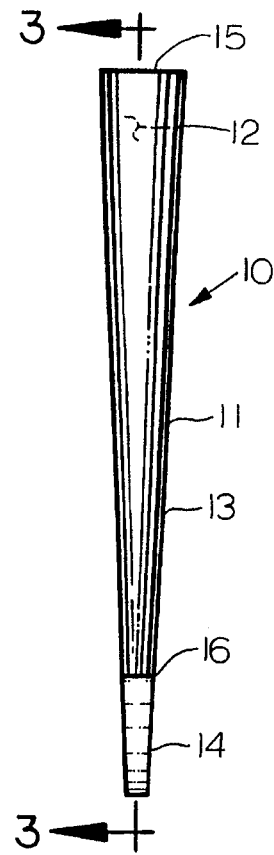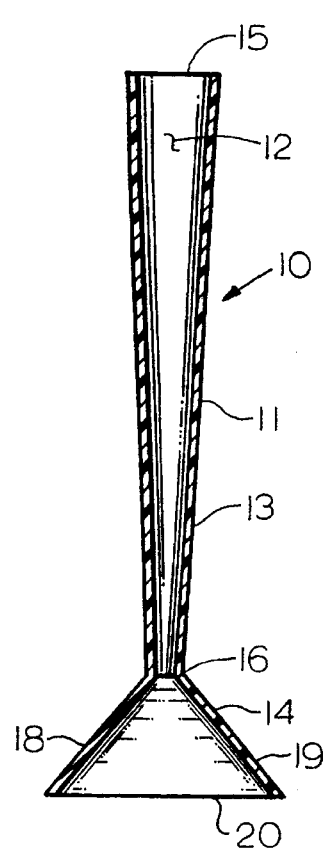
FIG. 1  FIG. 2  FIG. 3

FIG. 4  FIG. 5
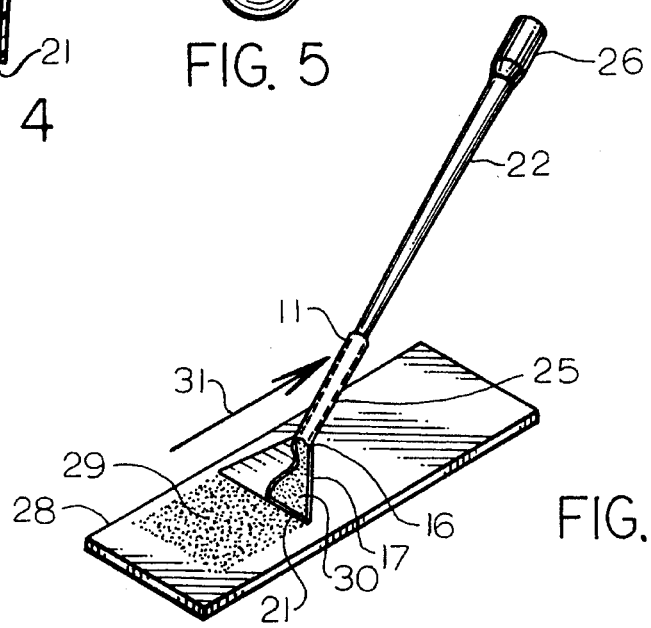
FIG. 7

SLIDE DISPENSING DEVICE AND METHOD

BACKGROUND

The present invention relates to the field of laboratory slide preparation. In particular it relates to cytology slide preparation. Also the fields of slide preparation for microbiology, hematology, special stains, and cytogenetics are contemplated.

The task of depositing a specimen on a slide for cytological examination has been the subject of some attention. It is desired to deposit the specimen spread thinly and evenly and in the case of some types of specimens, in a monolayer.

There has been considerable effort to improve cytology smear presentation. One aspect concentrates on the monolayered presentation of cells on the slide.

There are a number of different methods of preparing slides. One of these is called the pull-apart method. In this method, a specimen is placed on one slide and another slide is placed over the specimen. This spreads the specimen between the two slides. Then the slides are pulled apart by lateral parallel motion. Normally cells will be on both slides and either or both may be used as a diagnostic sample. This method is easy and inexpensive but gives inconsistent presentation results.

Preparation by cytocentrifugation and by membrane filtration are other techniques. A good review of the subject is found in the April 1991 issue of *American Clinical Laboratory* in an article entitled "Improved Technology For Cytology Specimen Preparation."

Along with various methods, various equipment has been designed which is primarily aimed at providing consistency in specimen presentation on slides.

The present invention is a method and device which accomplishes a reliable and controlled deposition of an even and thin specimen on a slide. They are particularly useful in preparing monolayer presentation on a slide.

SUMMARY OF THE INVENTION

The device, called a slide dispensing device, is formed with an interior passageway running through it. It has an upper portion which is a tapered tube, shaped so that a pipette tip can be nested to its interior surface, and a dispensing portion which is fan shaped and tapered to present a long narrow dispensing orifice. When a pipette is assembled by nesting in the upper portion, specimen material in the pipette can be dispensed from the pipette into the slide dispensing device and then further dispensed from the slide dispensing device onto a slide through the long narrow orifice. While being dispensed through the long narrow orifice, a specimen can be evenly spread onto a slide and in particular can be monolayered onto a slide.

The method employs the slide dispensing device and a standard pipette as described above. In the method, the pipette is used to pick up a specimen and is nested to the slide dispensing device. Then the slide dispensing device with the pipette nested to it is placed on a slide upper surface. The slide dispensing device is moved laterally across the slide as the pipette bulb is squeezed, so that the specimen will exit the long narrow dispensing orifice to form an evenly distributed and uniform specimen on the slide.

While the device and method are seen as especially useful in cytology slide preparation and particularly monolayer presentation, they are also applicable to slide preparation in the fields of microbiology, hematology, special stains, and cytogenetics. These specified areas are not intended to exclude other areas where predicable, reliable, uniform slide presentation is desired.

BRIEF DESCRIPTION OF DRAWINGS

FIG. 1 shows a front view of the slide dispensing device,

FIG. 2 shows a side view of the slide dispensing device.

FIG. 3 shows a section view of the slide dispensing device taken along 3—3 as shown in FIG. 2.

FIG. 4 shows a partial section view of a portion of the slide dispensing device taken along 4—4 as shown in FIG. 1.

FIG. 5 shows a bottom view of the slide dispensing device.

FIG. 7 shows the slide dispensing device combined with a nested pipette being used to deposit a specimen on a slide.

MODE(S) FOR CARRYING OUT THE INVENTION

Figure 6:
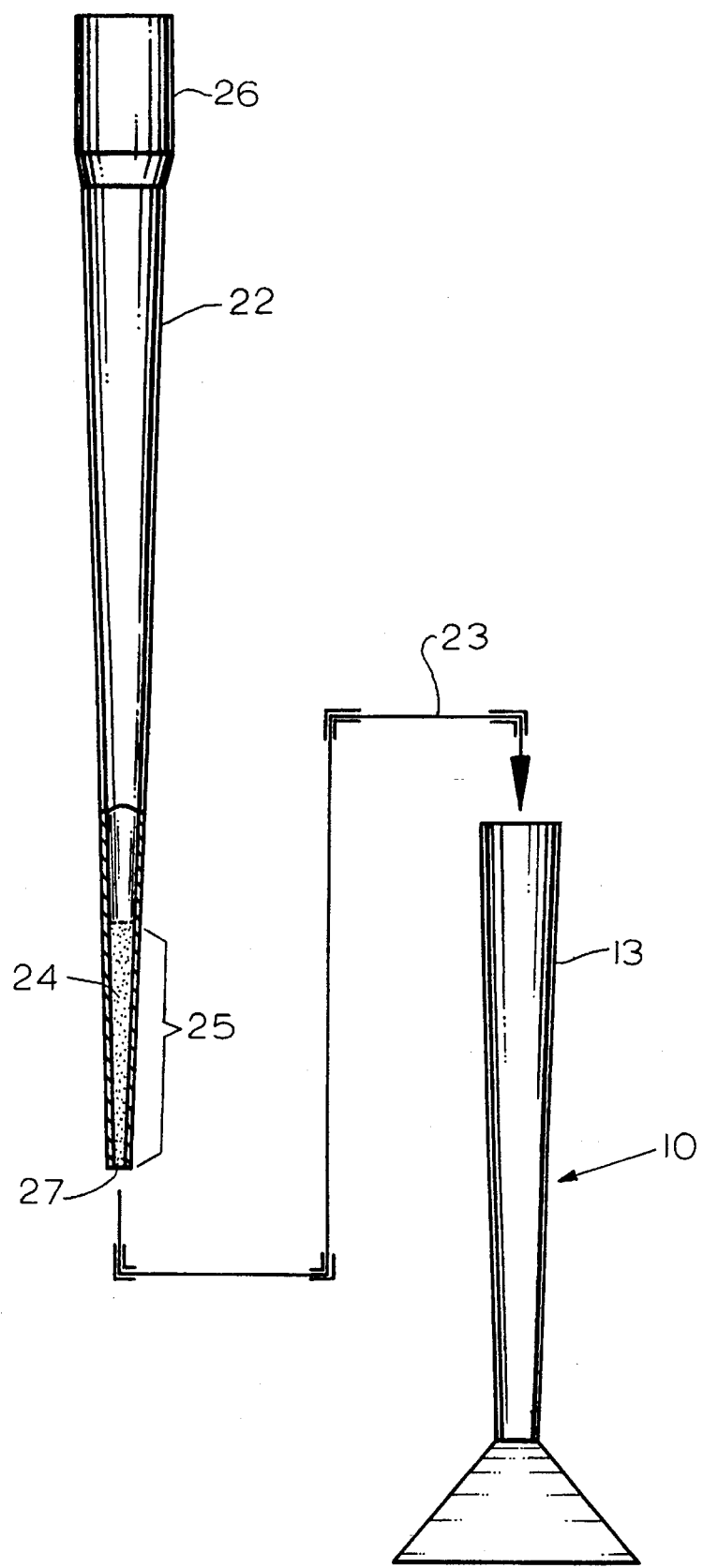
FIG. 6 shows a conventional cytology laboratory pipette and the slide dispensing device prior to nesting and indicating the nesting method.

Referring to FIGS. 1, 2, 3, 4, and 5, a slide dispensing device for preparing cytology slides in accordance with the present invention is generally indicated at 10. The device 10 preferably is formed of an integral body 11, for example, of a plastic material, that may be manufactured, for example, by molding. The plastic is preferably at least translucent to enable viewing of specimen material inside it as will be described below. The body 11 is formed of walls which define a hollow inner chamber 12 extending continuously through the body 11.

The body 11 includes an upper portion 13 and a lower portion 14. The upper portion 13 is in the shape of a cone which has an entry orifice 15. The upper portion terminates at a transition area 16, where a lower portion 17 begins. The lower portion 17 is fan shaped, being narrowest at the transition area 16 and expanding laterally along lateral sides 18 and 19 and terminating in a wide end 20 which defines a long narrow dispensing orifice 21 as seen best in FIGS. 3, 4 and 5.

The inner chamber 12 is open from the entry orifice 15 to the dispensing orifice 21.

FIG. 6 shows the slide dispensing device 10 adjacent to a conventional soft plastic cytology pipette 22, the line 23 indicated how the two will be assembled by inserting the pipette 22 to nest in the upper portion 13 of the body 11. As shown, a cytology specimen 24 is contained in the pipette. The pipette has a lower terminal portion generally indicated at 25, a bulb 26 and dispensing orifice 27.

As shown in FIG. 7 the lower terminal portion 25 of the pipette 22 is close to the lower portion 17 of the slide dispensing device 10, being close to the transition area 16. This closeness will ensure good flow of the specimen from the pipette 22 into the fan shaped lower portion 17 and consequently flowing out of the long narrow orifice 21.

FIG. 7 shows the assembled slide dispensing device 11 and pipette 22 being used to dispense a specimen onto a slide 27. Dispensing is accomplished by squeezing the pipette bulb 26. The specimen has been dispensed as shown at 29, and further specimen is available in the assembled pipette and slide dispensing device as shown at 30 for further dispensing.

As shown in FIG. 4, the preferred configuration of the lower portion 17 is to present an internal space which is narrowest at the long narrow dispensing orifice 21 and is gradually wider toward the transition area 16. This permits good even flow of the specimen by ensuring a slight pressure at the dispensing orifice 1 as the pipette bulb 26 is squeezed.

In a particular implementation, using a six inch soft plastic pipette, the slide dispensing device 10 will be about 2½" long, of which the fan shaped lower portion 17 will be about ⅜" long and the length of the wide end 20, about ¾ inch. These dimensions can be varied, for example to present the desired slide presentation smear width, and to receive the particular pipette of choice or to enable adequate nesting of a range of pipettte sizes.

In the method of the present invention, a cytology specimen is aspirated into a pipette 22 from the next prior step in dispensing of the specimen. While this practice of the present method proceeds after preparation of the specimen and may be considered to include the preparation steps, it is known that there are several methods and apparatus for such preparation and except as described below, this invention broadly includes any suitable preparation step which makes a specimen available which can be aspirated into a pipette, or a device equivalent to a pipette.

Once the specimen resides in the pipette 22, as seen in FIG. 6, the slide dispensing device 11 and the pipette 22 are nested to the position shown in FIG. 7.

Then, the slide dispensing device 11, as assembled with the pipette 22, is positioned in contact with a slide 27 as shown in FIG. 7, with one of the long edges forming the long narrow orifice 21 in contact with the slide 28. The slide dispensing device 11 and assembled pipette 22 are moved along the slide 28 as shown by the arrow 31. Simultaneously with this movement, the pipette bulb 26 is squeezed sufficiently to expel the specimen contained in it onto the slide. The slide dispensing device 11 is preferably tilted as shown in FIG. 7 to enable the specimen to flow readily out of the long narrow orifice 21 as it is dispensed onto the slide. A tilt of 45° works well.

The result is an even deposit of the specimen spread over the slide as shown at 29. It is important that the pipette 22 fit snugly into the upper portion 13 to effect a seal so that when the pipette 22 is squeezed the specimen can flow only out through the long narrow orifice 21 and so that an even pressure on the specimen is established and can be controlled by the user's pressure on the pipette bulb 26.

A modest amount of technique development on the part of a technician will enable use of the slide dispensing device 11, and of the method, for consistent preparation of evenly deposited specimen material over the slide with minimal overlap of cells to allow clear observation and optimal diagnostic accuracy. In particular proper coordination of pressure on the pipette bulb and sliding the slide dispensing device across the face of the slide will result in a band on specimen of even thickness and width, and where desired, resulting in a monolayer presentation.

The slide dispensing device 11 is of such simplicity and material that it is and should be disposable after use, as is the pipette 22.

Although the present invention has been described with reference to preferred embodiments, numerous modifications and rearrangements can be made with the equivalent result still crabraced within the scope of the invention.

What is claimed is:

1. A method of preparing a cytology slide specimen comprising;

providing a slide ready to receive a specimen;

providing a slide dispensing device comprising;

a hollow upper portion terminating at a first end in an upper opening and terminating at a second end in a lower opening to define a chamber and at least a portion thereof extending from the upper opening toward the lower opening being tapered and circular in cross section in order to receive the tip of a pipette;

a hollow lower portion extending from the second end of the upper portion in open communication with said chamber and terminating at a long narrow dispensing orifice;

inserting a pipette having a specimen therein to be spread onto the slide into the upper opening and contacting the outer surface of the pipette to the inner surface of the wall forming the upper portion of the slide dispensing device;

placing the slide dispensing device so that the long narrow orifice has its long dimension adjacently parallel to the surface of the slide;

dispensing the specimen from the pipette into the slide dispensing device and out the long narrow dispensing orifice;

while dispensing the specimen moving the slide dispensing device along the slide so as to allow the specimen to be dispensed uniformly over an area of the slide traversed by said movement.

2. The method of claim 1 wherein the slide dispensing device upper portion is tapered such that its inner surface will nestingly contact the outer surface of the pipette tip when the pipette tip is placed inside the upper portion.

3. The method of claim 1 further comprising;

providing a pipette having a lower terminal portion terminating in a dispensing orifice in which the lower terminal portion is insertable into the upper portion of the slide dispensing device.

4. The method of claim 3 wherein the pipette lower terminal portion is configured to sealingly fit into the upper portion of the slide dispensing device.

5. The method of claim 1 wherein at least a portion of said chamber extending from the upper opening toward the lower opening being tapered and circular in cross section in order the receive the pipette tip.

6. A slide dispensing device comprising;

a hollow upper portion terminating at a first end in an upper opening and terminating at a second end in a lower opening to define a chamber; and a hollow lower portion extending from the second end of the upper portion in open communications with said chamber and terminating at a long narrow dispensing orifice.

7. The slide dispensing device of claim 6 wherein the upper portion is tapered such that its inner surface will nestingly contact the outer surface of the pipette tip when the pipette tip is placed inside the upper portion.

8. The device of claim 6 further wherein at least a portion of said chamber extending from the upper opening toward the lower opening being tapered and circular in cross section.

9. A slide dispensing assembly comprising;

a slide dispensing device comprising;

a hollow upper portion terminating at a first end in an upper opening and terminating at a second end in a lower opening to define a chamber; and a hollow lower portion extending from the second end of the upper portion in open communications with said chamber and terminating at a long narrow dispensing orifice; and a pipette having a lower terminal portion terminating in a dispensing orifice said lower terminal portion being insertable into the upper portion of the slide dispensing device.

10. The assembly of claim 9 wherein the pipette lower terminal portion is configured to sealingly fit into the upper portion of the slide dispensing device.

11. The assembly of claim 9 further wherein at least a portion of said chamber extending from the upper opening toward the lower opening being tapered and circular in cross section in order to receive the tip of a pipette.

12. The device of claim 11 wherein the said chamber is tapered to nestingly contact the outer surface of the pipette tip when the pipette tip is placed inside the chamber.

13. A slide dispensing device for use in combination with a dispensing pipette of the type having a tapered circular dispensing tip terminating in an orifice comprising;

a hollow upper portion terminating at a first end in an upper opening and terminating at a second end in a lower opening to define a chamber and at least a portion thereof extending from the upper opening toward the lower opening being tapered and circular in cross section in order to receive the pipette tip; and a hollow lower portion extending from the second end of the upper portion in open communication with said chamber and terminating at a long narrow orifice.

14. The device of claim 13 wherein the said chamber is tapered to nestingly contact the outer surface of a pipette tip when a pipette tip is placed inside the chamber.

* * * * *